(12) United States Patent
Ahsan et al.

(10) Patent No.: US 12,731,237 B2
(45) Date of Patent: Sep. 8, 2026

(54) SYSTEM AND METHOD FOR FACIAL MASK DETECTION AND DISINFECTION FOR REUSE

(71) Applicants: Hamad Medical Corporation, Doha (QA); Synaptic Vanguard WLL, Doha (QA)

(72) Inventors: Nazmul Ahsan, Doha (QA); Shidin Balakrishnan, Doha (QA); Sarada Prasad Dakua, Doha (QA); Abdulla Al-Ansari, Doha (QA); Julien Abi Nahed, Doha (QA); Joji Abraham, Doha (QA); Carlos Velasquez, Doha (QA)

(73) Assignee: HAMAD MEDICAL CORPORATION, Doha (QA)

( * ) Notice: Subject to any disclaimer, the term of this patent is extended or adjusted under 35 U.S.C. 154(b) by 123 days.

(21) Appl. No.: 18/697,691

(22) PCT Filed: Oct. 5, 2022

(86) PCT No.: PCT/QA2022/050019
§ 371 (c)(1),
(2) Date: Apr. 1, 2024

(87) PCT Pub. No.: WO2023/059211
PCT Pub. Date: Apr. 13, 2023

(65) Prior Publication Data

US 2024/0289935 A1 Aug. 29, 2024

Related U.S. Application Data

(60) Provisional application No. 63/252,382, filed on Oct. 5, 2021.

(51) Int. Cl.
*G06T 7/00* (2017.01)
*A61L 2/10* (2026.01)
(Continued)

(52) U.S. Cl.
CPC .............. *G06T 7/0002* (2013.01); *A61L 2/10* (2013.01); *A61L 2/24* (2013.01); *B07C 5/342* (2013.01);
(Continued)

(58) Field of Classification Search
CPC ..................... G06T 7/0002; G06T 7/73; G06T 2207/20084; A61L 2/10; A61L 2/24;
(Continued)

(56) References Cited

U.S. PATENT DOCUMENTS

2008/0083411 A1 4/2008 Guth
2011/0005342 A1* 1/2011 Treat ..................... G16H 40/40 414/754
(Continued)

FOREIGN PATENT DOCUMENTS

WO 2018087225 A1 5/2018

OTHER PUBLICATIONS

USA Health | USA Health conserving N95 masks with UV-C light sterilization | Apr. 28, 2020 | Lindsay Mott | https://www.usahealthsystem.com/news/conserving-n95-masks-with-uv-c-light-sterilization#:~:text=To%20disinfect%20the%20masks%2C%20USA,the%20sun%20damages%20skin%20cells. (Year: 2020).*
(Continued)

*Primary Examiner* — Ramon A. Mercado
*Assistant Examiner* — John Martin O'Malley
(74) *Attorney, Agent, or Firm* — K&L Gates LLP

(57) ABSTRACT

The present disclosure generally relates to systems and methods for handling, inspecting, and orienting a mask to be placed into a disinfection system. The systems and methods include a computer vision system configured to detect the mask position and calculate an orientation angle of the mask, a first robotic arm configured to lift the mask and adjust the mask position based on the orientation angle, and a second
(Continued)

robotic arm configured to hold open the mask for a visual inspection of an internal and an external surface of the mask.

16 Claims, 9 Drawing Sheets

(51) Int. Cl.

| | |
|---|---|
| ***A61L 2/24*** | (2006.01) |
| ***A61L 103/50*** | (2026.01) |
| ***B07C 5/342*** | (2006.01) |
| ***B25J 9/00*** | (2006.01) |
| ***B25J 9/16*** | (2006.01) |
| ***G06T 7/73*** | (2017.01) |
| ***G06V 10/44*** | (2022.01) |
| ***G06V 10/764*** | (2022.01) |
| ***G06V 20/50*** | (2022.01) |

(52) U.S. Cl.

CPC ........... *B25J 9/0093* (2013.01); *B25J 9/1682* (2013.01); *B25J 9/1697* (2013.01); *G06T 7/73* (2017.01); *G06V 10/44* (2022.01); *G06V 10/764* (2022.01); *G06V 20/50* (2022.01); *A61L 2103/50* (2026.01); *A61L 2202/14* (2013.01); *B07C 2501/0063* (2013.01); *G06T 2207/20084* (2013.01); *G06V 2201/06* (2022.01)

(58) Field of Classification Search

CPC . A61L 2202/14; A61L 2202/26; B07C 5/342; B07C 2501/0063; B25J 9/0093; B25J 9/1682; B25J 9/1697; B25J 9/0084; B25J 11/0085; G06V 10/44; G06V 10/764; G06V 20/50; G06V 2201/06; G05B 2219/39571

See application file for complete search history.

(56) References Cited

U.S. PATENT DOCUMENTS

| | | | | |
|---|---|---|---|---|
| 2015/0224650 | A1 | 8/2015 | Xu et al. | |
| 2017/0172398 | A1 | 6/2017 | Carlson | |
| 2019/0389070 | A1 | 12/2019 | Sirkett | |
| 2021/0290799 | A1* | 9/2021 | Zhong | A61L 2/14 |
| 2021/0353792 | A1* | 11/2021 | McCall | A61L 2/07 |
| 2021/0402026 | A1* | 12/2021 | Dobrovolsky | A61L 2/10 |
| 2022/0351357 | A1* | 11/2022 | Waldron | G06T 7/0002 |
| 2023/0201389 | A1* | 6/2023 | Tansu | A61L 2/26 422/24 |
| 2023/0277700 | A1* | 9/2023 | Amir | A61L 2/24 250/455.11 |

OTHER PUBLICATIONS

RobotPhoenix | https://www.youtube.com/watch?v=LBIS295m7dM | delta robot pick place disposable face mask/dust mask auto feeding for packing machine | Feb. 10, 2020 (Year: 2020).*

International Search Report for related International Application No. PCT/QA2022/050019; action dated Apr. 13, 2023; (2 pages).

Written Opinion for related International Application No. PCT/QA2022/050019; action dated Apr. 13, 2023; (4 pages).

Extended European Search Report for related European Application No. 22879001.0; action dated Jul. 10, 2025; (11 pages).

Swensen; “Robot allows clinicians to reuse thousands of masks in the COVID-19 fight”; Medical press; Apr. 2020; 4 pages).

* cited by examiner

SYSTEM AND METHOD FOR FACIAL MASK DETECTION AND DISINFECTION FOR REUSE

CROSS-REFERENCE TO RELATED APPLICATION

This application is a National Stage filing under 35 U.S.C. 371 of International Application No. PCT/QA2022/050019, filed Oct. 5, 2022, which claims priority to and the benefit of U.S. Provisional Patent Application No. 63/252,382 filed Oct. 5, 2021, the entire contents of which are incorporated by reference herein.

BACKGROUND

A KN-95 mask can be used multiple times after undergoing an appropriate disinfection process. Typically, the masks come in a closed orientation and the straps are folded irregularly. If the mask is disinfected with Ultraviolet Germicidal Irradiation (UVGI), the placing and orientation of mask in the radiation system bears significant importance. If the masks are placed in a closed position, the UV Radiation will not be able to efficiently reach all the regions within the mask and there will be shadow effects. Furthermore, direct human handling of infected masks is unsafe due to a high risk of infection. This increases the burden on healthcare infrastructure due to avoidable infections and subsequent delivery of care. Techniques for infection mitigation become ever more expensive when humans are dealing with this process because extra care and safety precaution need to be taken in the form of safety equipment and stringent, longer infection control protocols.

SUMMARY

The present disclosure generally relates to a system and method for inspecting, handling, and loading facial masks in an open position so that the mask may be disinfected and reused.

In light of the present disclosure, and without limiting the scope of the disclosure in any way, in a first aspect of the present disclosure, which may be combined with any other aspect listed herein unless specified otherwise, a system for handling, inspecting, and orienting a mask to be placed into a disinfection system. The system comprising a computer vision system configured to detect the mask position and calculate an orientation angle of the mask. The system further comprises a first robotic arm configured to lift the mask and adjust the mask position based on the orientation angle, and a second robotic arm configured to hold open the mask for a visual inspection of an internal and an external surface of the mask.

In accordance with a second aspect of the present disclosure, which may be used in combination with any other aspect listed herein unless stated otherwise, wherein the computer vision system comprises a plurality of cameras, and wherein the visual inspection of the internal and the external surfaces are performed by the plurality of cameras while the mask is held open in a fixed position.

In accordance with a third aspect of the present disclosure, which may be used in combination with any other aspect listed herein unless stated otherwise, the system further comprising a form correction fixture configured to stretch and open the mask by applying tension to straps on the mask while supporting a portion of the internal surface with a conical fixture.

In accordance with a forth aspect of the present disclosure, which may be used in combination with any other aspect listed herein unless stated otherwise, wherein the mask is transferred in a generally flat condition along a conveyor to the first robotic arm.

In accordance with a fifth aspect of the present disclosure, which may be used in combination with any other aspect listed herein unless stated otherwise, wherein the computer vision system is further configured to classify visual parameters of the mask, wherein the visual parameters comprise at least one of impurities, punctures, nose clip damage, and strap damage.

In accordance with a sixth aspect of the present disclosure, which may be used in combination with any other aspect listed herein unless stated otherwise, wherein the computer vision system is further configured to analyze the mask to determine whether the mask can be re-used without human intervention.

In accordance with a seventh aspect of the present disclosure, which may be used in combination with any other aspect listed herein unless stated otherwise, wherein the second robotic arm is further configured to place masks that can be re-used in an open position for transfer to the disinfection system and configured to place masks that cannot be re-used onto a rejection conveyor for transfer to a rejection bin.

In accordance with a eighth aspect of the present disclosure, which may be used in combination with any other aspect listed herein unless stated otherwise, wherein the computer vision system is further configured to identify a nose piece and a strap using object detection algorithms and configured to apply at least one of a nose mask or a strap mask to omit image details from analysis.

In accordance with a ninth aspect of the present disclosure, which may be used in combination with any other aspect listed herein unless stated otherwise, wherein the computer vision system is further configured to circumscribe a circle around a perimeter of the mask, identify a key point along the perimeter and a key line between a center of the circle and the key point, wherein a direction of the key line is related to the orientation angle of the mask.

In accordance with a tenth aspect of the present disclosure, which may be used in combination with any other aspect listed herein unless stated otherwise, a method for handling, inspecting, and orienting a mask to be placed into a disinfection system. The method comprising detecting the mask position and calculating an orientation angle of the mask with a computer vision system, lifting the mask with a first robotic arm and adjusting the mask position based on the orientation angle, holding the mask open with a second robotic arm, and visually inspecting an internal and an external surface of the mask.

In accordance with an eleventh aspect of the present disclosure, which may be used in combination with any other aspect listed herein unless stated otherwise, wherein visually inspecting the internal and the external surfaces is performed by a plurality of cameras, and wherein the mask is held open in a fixed position during the visual inspection.

In accordance with a twelfth aspect of the present disclosure, which may be used in combination with any other aspect listed herein unless stated otherwise, the method further comprising supporting a portion of the internal surface of the mask with a conical fixture, and applying tension to straps of the mask to stretch and open the mask.

In accordance with a thirteenth aspect of the present disclosure, which may be used in combination with any other aspect listed herein unless stated otherwise, the method further comprising transferring the mask in a generally flat condition along a conveyor to the first robotic arm.

In accordance with a fourteenth aspect of the present disclosure, which may be used in combination with any other aspect listed herein unless stated otherwise, the method further comprising classifying visual parameters of the mask with the computer vision system, wherein the visual parameters comprise at least one of impurities, punctures, nose clip damage, and strap damage.

In accordance with a fifteenth aspect of the present disclosure, which may be used in combination with any other aspect listed herein unless stated otherwise, the method further comprising analyzing the mask with the computer vision system and without human intervention to determine whether the mask can be re-used.

In accordance with a sixteenth aspect of the present disclosure, which may be used in combination with any other aspect listed herein unless stated otherwise, the method further comprising using the second robotic arm to place masks that can be re-used in an open position for transfer to the disinfection system, and using the second robotic arm to place masks that cannot be re-used onto a rejection conveyor for transfer to a rejection bin.

In accordance with a seventeenth aspect of the present disclosure, which may be used in combination with any other aspect listed herein unless stated otherwise, the method further comprising identifying a nose piece and a strap using the computer vision system and object detection algorithms, and applying at least one of a nose mask or a strap mask to omit image details from analysis.

In accordance with an eighteenth aspect of the present disclosure, which may be used in combination with any other aspect listed herein unless stated otherwise, the method further comprising circumscribing a circle around a perimeter of the mask within the computer vision system, identifying a key point along the perimeter and a key line between a center of the circle and the key point, and calculating the orientation angle of the mask based on a direction of the key line.

The reader will appreciate the foregoing details, as well as others, upon considering the following detailed description of certain non-limiting embodiments including a system and method for inspecting and loading masks in an open position for disinfection. The advantages discussed herein may be found in one, or some, and perhaps not all of the embodiments disclosed herein.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION

The present disclosure generally relates to a system and method for detecting and disinfecting a facial mask for reuse.

In the present disclosure, a novel technique of implementing robotic manipulators for handling used masks prior to the loading of a conveyor belt for disinfection with UVGI is proposed. The disclosure provides a consistent method of inspecting, handling, and loading the used masks in an open position for disinfection. The disclosure provides systems and methods that allow for large quantities of masks to be processed autonomously while providing consistent and reliable disinfection to reduce the potential spread of infection. During the sterilization with Ultraviolet C (“UVC”) light radiation, the mask is fixed in the open position as established by the robotic manipulators, and the disinfection process can be conducted with high efficacy.

Aspects of the present disclosure may provide a software based solution to autonomously identify masks placed on a platform, autonomously perform a “pick and place” maneuver using robotic manipulators from a loading platform onto a form correction fixture in the open position, and use Artificial Intelligence (AI) algorithms to independently analyze different physical parameters of the mask placed in the open inspection position to verify if the detected mask can proceed to disinfection.

Aspects of the present disclosure may provide automated approaches to recycle for example K-95 or N-95 face masks, which can result in reducing the cost and environmental impact of face mask production and can also contribute to solving the problem of mask shortage faced by many countries.

According to an embodiment of the present disclosure, a system and method for inspecting, handling, and disinfecting a facial mask for reuse is provided.

Figure 1:
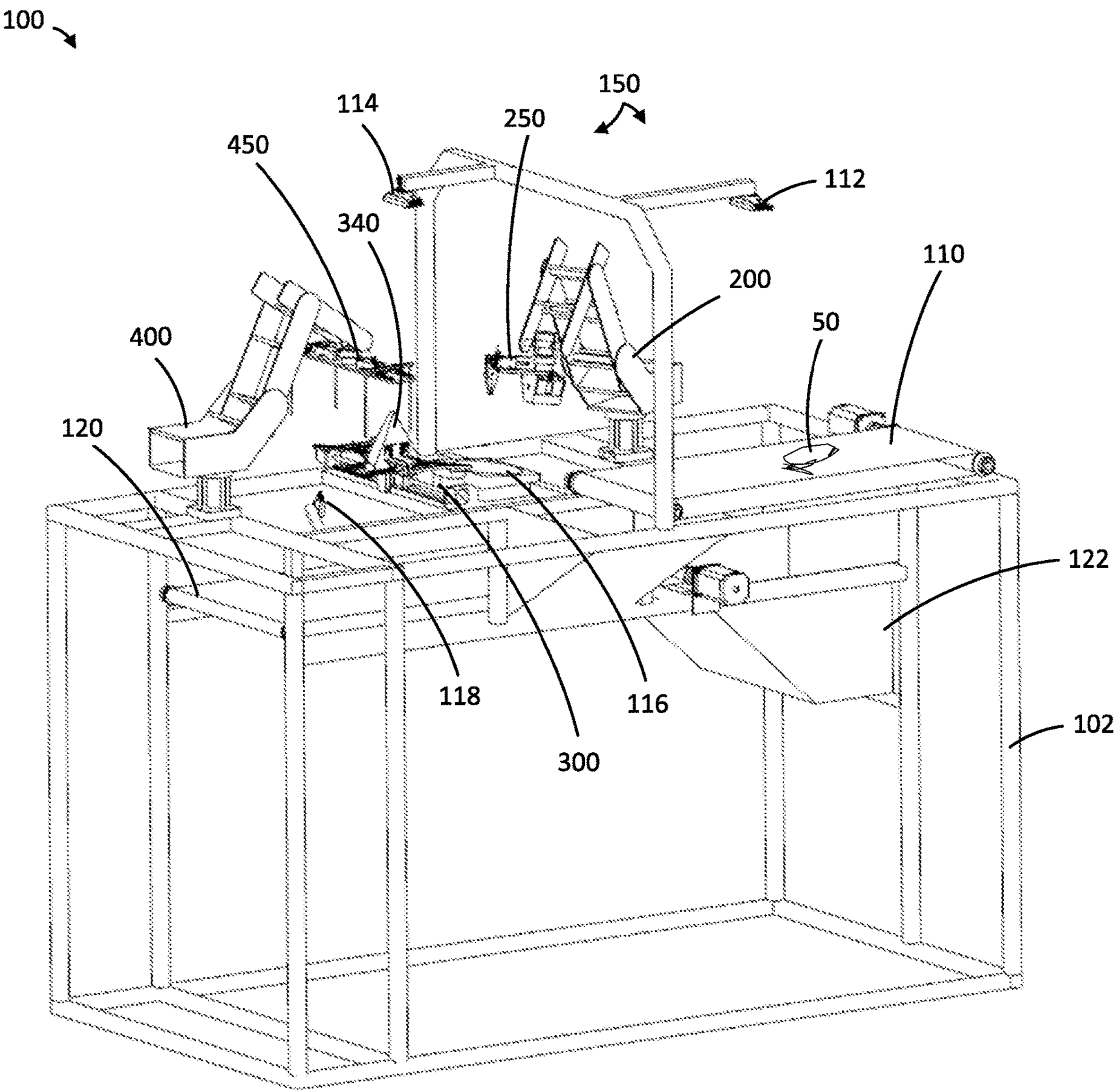
FIG. 1 is an isometric view of a system for handling and orienting a mask to be placed into a disinfection system, according to one or more embodiments.

Referring to FIG. 1, a robotic manipulator system 100 (more generally referred to as “system 100”) is shown that may be used for handling, inspecting, and orienting a mask to be placed into a disinfection system (not shown). Together the processes of handling, inspecting, and orientating may alternatively be referred to together as “processing”. The system 100 comprises a base 102 supporting a conveyor 110 that may be loaded with one or more used masks 50. The example of FIG. 1 shows one mask 50, but a plurality of masks 50 may also be loaded on the conveyor 110 for sequential processing. During operation of the conveyor 110, the mask 50 is transferred along the length of the conveyor 110 to a first robotic arm 200 that may be configured to capture and lift the mask 50 from the conveyor 110. The masks 50 are loaded onto the conveyor 110 in a generally flat condition whereby one external surface of the mask 50 rests on the conveyor 110 surface while the other opposing external surface faces generally upward. Because the masks 50 have been used, the relaxed shape of the masks 50 varies from one mask 50 to the next and thus the upward facing surface may or may not be precisely parallel to the surface of the conveyor 110. The masks 50 may be placed onto the conveyor 110 in a generally random angular orientation and thus the system 100 may be configured to adjust to any angular orientation as described further herein. A camera 112 of a computer vision system 150 is used to visually determine the position and angular orientation of the mask 50 on the conveyor 110. The speed of the conveyor 110 is held constant in the example of FIG. 1 and thus the computer vision system 150 can determine the position and orientation of the mask 50 while the mask 50 is in motion.

Figure 2A:
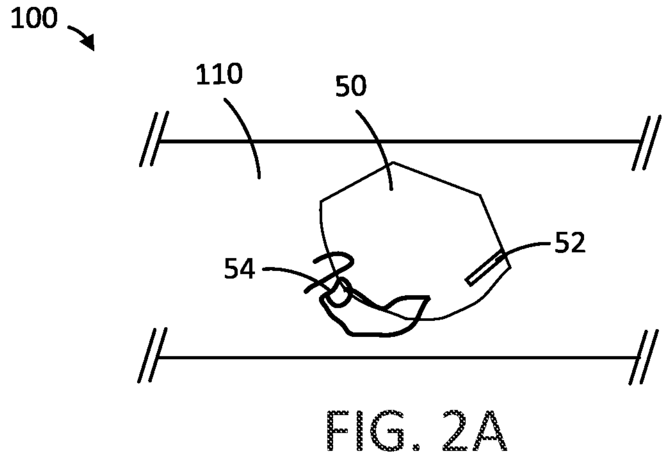
FIG. 2A is a partial top view of the system of FIG. 1, showing a mask resting on the conveyor.
Figure 2B:
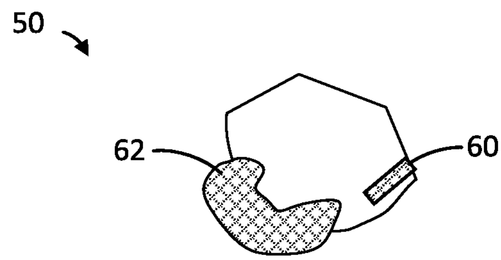
FIG. 2B is the partial top view of FIG. 2A with the conveyor omitted for clarity and masking added to portions of the mask.
Figure 2C:
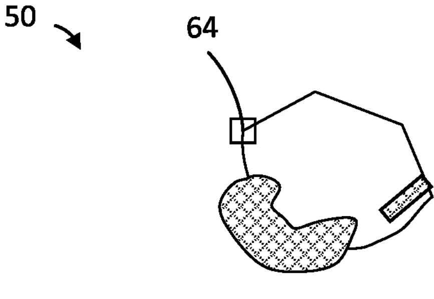
FIG. 2C is another partial top view of FIG. 2A with a key point identified on the mask.
Figure 2D:
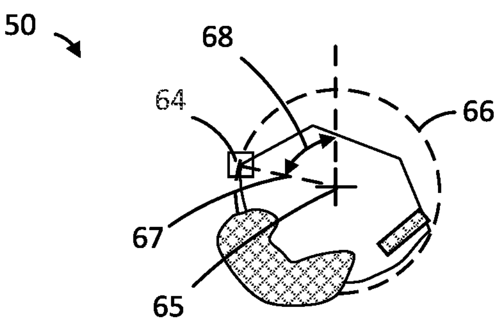
FIG. 2D is another partial top view of FIG. 2A with an orientation angle for the key point determined.

Referring to FIG. 2A, a top view of a portion of the conveyor 110 is shown as may be captured with the camera 112 of the computer vision system 150. The mask 50 is shown from a side view and comprises a nose piece 52 and a strap 54. FIG. 2B shows the same view of the mask 50 as shown in FIG. 2A and omits the conveyor 110 for clarity. When analyzing the image from the camera 112, the computer vision system 150 is configurable to identify the nose piece 52 and the strap 54 using object detection algorithms. The computer vision system 150 then applies a nose mask 60 and a strap mask 62 to omit image details of the nose piece 52 and the strap 54, respectively. An additional mask (not shown) may also be placed around the perimeter of the mask 50 to omit details from the surface of the conveyor 110 as needed. As shown in FIG. 2C, a key point 64 is identified by the computer vision system 150 at the corner of the mask 50 opposite the nose mask 60. The key point 64 serves as an angular position reference and thus any other defined and fixed point along the perimeter of the mask 50 could alternatively be used. For example, the angular corner adjacent to the nose mask 60 could be used or the angular corner adjacent the key point 64 could be used. In some embodiments, the key point 64 as shown in FIG. 2C may be used because the key point 64 coincides with the fold at the point of transition between the internal and external surface of the mask 50 and is most reliably identified as a sharp corner even in heavily used and worn masks 50. Referring to FIG. 2D, the computer vision system 150 then fits a minimum enclosing circle to the perimeter of the mask 50 (e.g., circumscribes the portions of the perimeter of the mask 50 not omitted by the nose mask 60 and the strap mask 62). The center of the resulting circumscribed circle is defined as a circle center 65 and a key line 67 is constructed between the circle center 65 and the key point 64. The angle between the key line 67 and a constant and known datum (such as the vertical line shown in FIG. 2D) then defines an angular orientation of the mask 50 as shown by an orientation angle 68. By visually measuring the orientation angle 68, the first robotic arm 200 can then impart an angular rotation to each mask 50 after lifting the mask 50 from the conveyor 110.

Referring again to FIG. 1, the first robotic arm 200 rests on a rotating base and comprises two or more segmented arms that allow the first robotic arm 200 to extend between the conveyor 110 and a loading platform 116. The loading platform 116 is stationary and thus positional encoders (not shown) may be used to guide the motion of the first robotic arm 200 to the loading platform 116. However, because the position of the mask 50 may vary along the width or length of the conveyor 110, the motion of the first robotic arm 200 may be also or alternatively be guided by the computer vision system 150 to adjust for the variable mask 50 position. The control of the first robotic arm 200 may be directly controlled with feedback from the computer vision system 150. Alternatively, the signal from computer vision system 150 may be used to calculate a distance and a position of the mask 50, and the first robotic arm 200 may remain in displacement control via the positional encoders. By either method, the first robotic arm 200 may be configured to capture and lift the mask 50 from the conveyor 110 and impart an angular rotation to the mask 50 so that the mask 50 is placed onto the loading platform 116 in a substantially consistent (e.g., from one mask 50 to the next mask 50) position and angular orientation.

Figure 3:
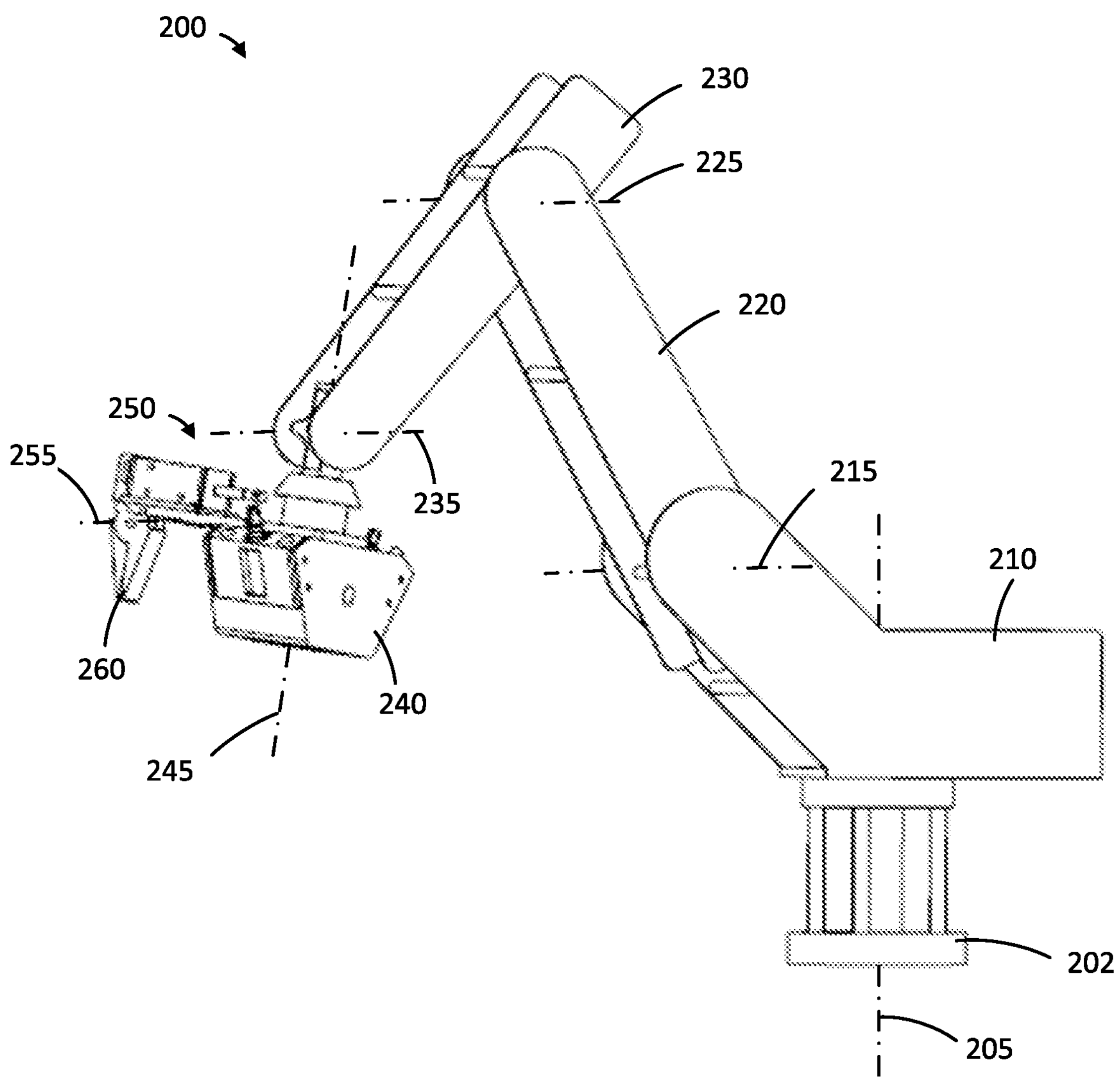
FIG. 3 is an isometric view of a robotic arm that may be used with the system of FIG. 1.

Referring to FIG. 3, the components comprising the first robotic arm 200 are shown in closer detail. In particular, the first robotic arm 200 comprises a base 202, a lower arm 210, a middle arm 220, an upper arm 230, and a first end effector 250 that is used in various modes to grip the mask 50. The base 202 rotatably couples to the base 102 (of the system 100 in FIG. 1) or rotatably couples to the lower arm 210, in each case allowing rotation of the lower arm 210 about an axis 205. The lower arm 210 and the middle arm 220 are pivotally hinged about an axis 215, the middle arm 220 and the upper arm 230 are pivotally hinged about an axis 225, and the upper arm 230 and the first end effector 250 are pivotally hinged about an axis 235. In addition, the first end effector 250 may also independently rotate in 360-degrees about an axis 245. In this manner, the first robotic arm 200 has an adjustable distance reach away from the base 202 fixed position, can translate the mask 50 in any of the six possible directions, and can rotate the mask 50 in 360-degrees at any position. The first end effector 250 comprises two separately operable solenoid powered grippers. In particular, the first end effector 250 comprises a needle gripper 240 and a scissor gripper 260 that hinges around an axis 255. Due to the nominally flat orientation of the mask 50 when on the conveyor 110, the needle gripper 240 is used for the mask 50 transfer between the conveyor 110 and the loading platform 116. After placing the mask 50 with the needle gripper 240, the scissor gripper 260 is then used to lift the mask 50 for transfer from the loading platform 116 to a conical fixture 340 of a form correction fixture 300 as shown in FIGS. 1 and 4.

Figure 4:
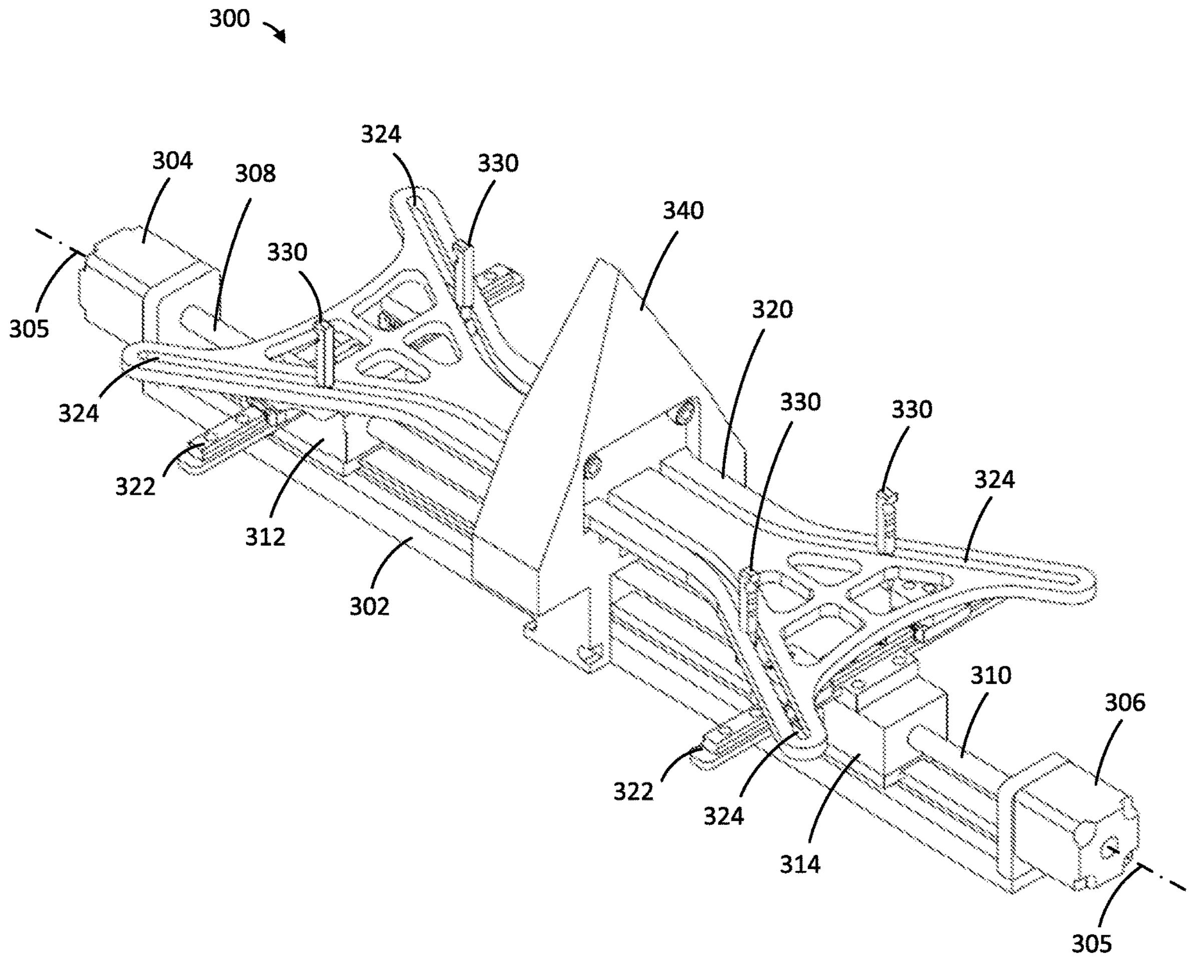
FIG. 4 is an isometric view of a robotic manipulator system that may be used with the system of FIG. 1.

Referring to FIG. 4, as the mask 50 is transferred to the conical fixture 340, the orientation of the mask 50 is transitioned from horizontal to vertical such that the seam between the two halves of the mask 50 faces substantially upward. When installed on the conical fixture 340, the straps 54 of the mask 50 hang on each side of the conical fixture 340 and surround four holding pins 330 that are retracted proximate to the conical fixture 340. Generally speaking, during operation of the form correction fixture 300, the holding pins 330 are operable to synchronously extend out and away from the conical fixture 340, thereby contacting and pulling outward on the straps 54 of the mask 50 and spreading open the shape of the mask 50. The synchronous motion of the holding pins 330 can be achieved by many mechanisms and linkages and thus this disclosure shall not be limited by the specific example of FIG. 4. In FIG. 4, the form correction fixture 300 comprises two opposing stepper motors 304, 306 each coupled to a base 302 and to a lead screw 308, 310, respectively that are aligned along an axis 305. The lead screw 308 threadably engages with a slide block 312 and the lead screw 310 threadably engages with a slide block 314. During operation of the stepper motors 304, 306, the lead screws 308, 310 rotate relative to the non-rotating slide blocks 312, 314 and opposing sliding motion is imparted to the slide blocks 312, 314. Two of the holding pins 330 are coupled to each of the slide blocks 312, 314 so that the holding pins 330 move with the slide blocks 312, 314 away from the conical fixture 340. A transverse rail 322 couples between each of the holding pins 330 and the slide blocks 312, 314 such that each holding pin 330 is capable of independent motion transverse to the axis 305. A stationary pin guide 320 comprising a plurality of slots 324 is used to guide the specific motion path of the holding pins 330 as the stepper motors 304, 306 operate to spread the holding pins 330 away from the conical fixture 340. More specifically, each slot 324 is sized to accept a holding pin 330 therethrough and provides a slidable coupling with each holding pin 330. In the example of FIG. 4, as the holding pins 330 move away from the conical fixture 340, the slots 324 guide the holding pins 330 to first move axially relative to the axis 305 and then guide the holding pins 330 to move at an angle relative to the axis 305 (e.g., move both axially away from the conical fixture 340 and transversely away from the axis 305). The stepper motors 304, 306 are operated until the straps 54 are sufficiently stretched and tensioned to flex the mask 50 into an open position. Load or torque on the stepper motors 304, 306 may be controlled to achieve a consistent stretch or tension along the straps 54 or displacement control may be used. For example, the stepper motors 304, 360 may be controlled to impart a particular number of rotations to translate the slide blocks 312, 314 and hence the holding pins 330 to a consistent position.

Referring again to FIG. 1, after the form correction fixture 300 opens the mask 50 into an open position, a second end effector 450 of a second robotic arm 400 is used to lift the mask 50 off of the form correction fixture 300 as the mask 50 remains in the open position. Similar to the first robotic arm 200 previously described, the second robotic arm 400 mounts to the base 102 of the system 100 via a rotating base and comprises two or more segmented arms that allow the second robotic arm 400 to extend to a plurality of positions. In the example of FIG. 1, the second robotic arm 400 is configured to extend between the form correction fixture 300, a position in view of the computer vision system 150, a rejection conveyor 120, and a position where the mask 50 may be placed on a main conveyor belt (not shown) to transfer the masks 50 to a sterilizer.

Each of the positions the second robotic arm 400 moves between are nominally stationary and thus positional encoders (not shown) may be used to guide the motion as needed. In situations where the form correction fixture 300 has spread the straps 54 of the mask 50 to a larger extent (e.g., larger sized masks or masks with worn or damaged straps 54), the positional encoders of the form correction fixture 300 can also be used to guide the spreading motion and position of the second end effector 450 as the second end effector 450 is used to lift the mask 50. In addition or alternatively, portions of the motion of the second end effector 450 or the second robotic arm 400 may be guided by the computer vision system 150 (e.g., to adjust for a variable mask 50 size or position). The control of the second robotic arm 400 may be directly controlled with feedback from the computer vision system 150. Alternatively, the signal from computer vision system 150 may be used to calculate a distance and position of the mask 50, and the second robotic arm 400 may remain in displacement control via the positional encoders. By either method, the second robotic arm 400 may be configured to lift the mask 50 from the form correction fixture 300 and move the mask between the plurality of positions previously described.

Figure 5:
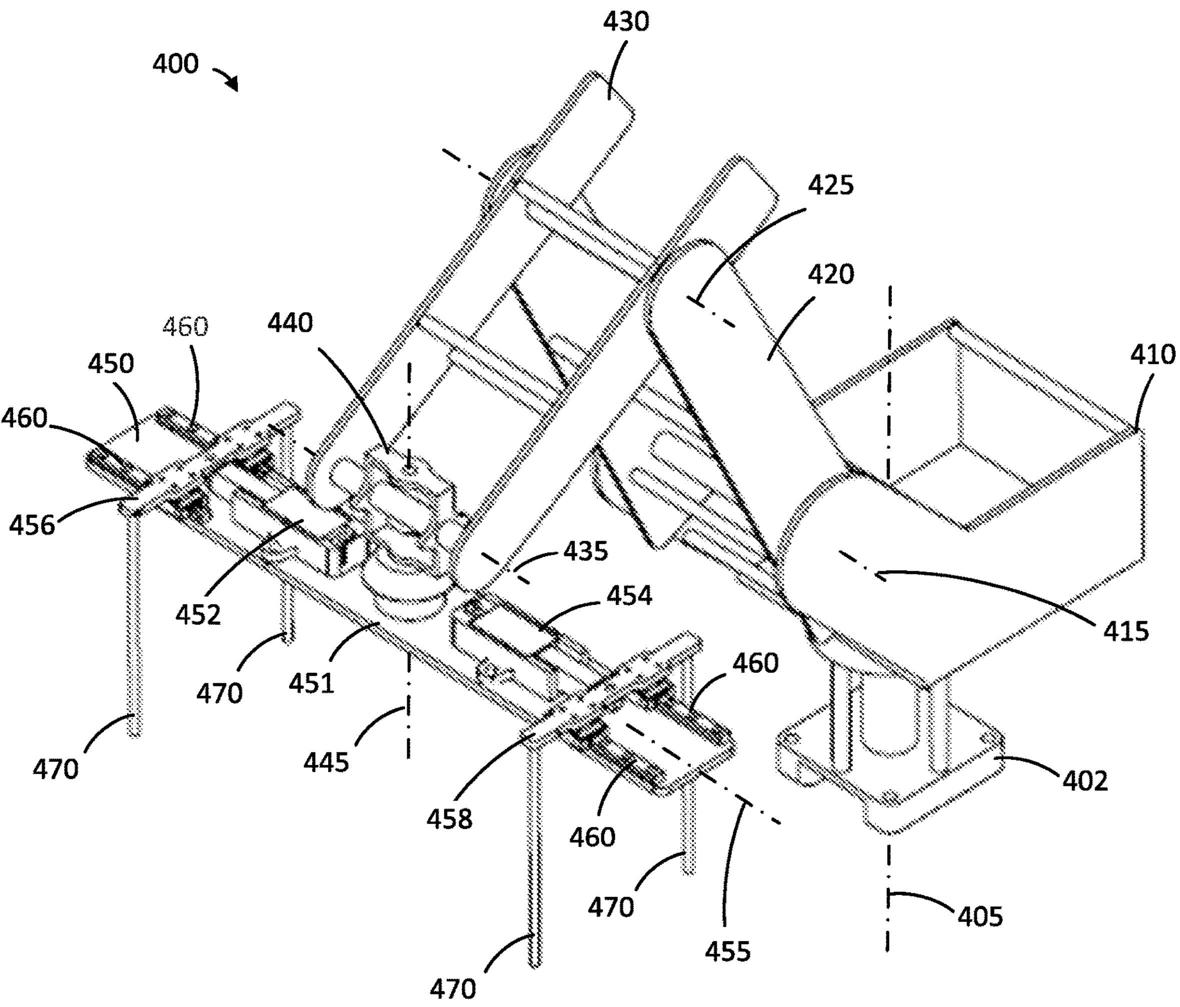
FIG. 5 is an isometric view of a form correction fixture that may be used with the system of FIG. 1.

Referring to FIG. 5, the components comprising the second robotic arm 400 are shown in closer detail. In particular, the second robotic arm 400 comprises a base 402, a lower arm 410, a middle arm 420, an upper arm 430, and the second end effector 450. The base 402 rotatably couples to the base 102 (of the system 100 in FIG. 1) or rotatably couples to the lower arm 410, in each case allowing rotation of the lower arm 410 about an axis 405. The lower arm 410 and the middle arm 420 are pivotally hinged about an axis 415, the middle arm 420 and the upper arm 430 are pivotally hinged about an axis 425, and the upper arm 430 and the second end effector 450 are pivotally hinged about an axis 435. In addition, the second end effector 450 may also independently rotate 360 degrees about an axis 445 via rotation of a knuckle 440. In this manner, the robotic manipulator system 400 has an adjustable distance reach away from the base 402 fixed position, can translate the mask 50 in any of the six possible directions, and can rotate the mask 50 in 360 degrees at any position. The second end effector 450 comprises a base plate 451, a linear actuator 452, a linear actuator 454, a cross bracket 456, a cross bracket 458, a plurality of slides 460, and a plurality of mask strap holding rods 470. Generally speaking, the plurality of mask strap holding rods 470 are held mutually parallel to one another and are used by the second end effector 450 to lift the mask 50 away from the form correction fixture 300, while the mask 50 remains in the open position.

The configuration and motion of the mask strap holding rods 470 can be achieved by many mechanisms and linkages and thus this disclosure shall not be limited by the specific example of FIG. 5. In FIG. 5, the linear actuators 452, 454 are coupled to the base plate 451 and are aligned with an axis 455 to allow sliding motion parallel to the axis 455, both towards and away from the axis 445 as the linear actuators 452, 454 are operated. The linear actuators 452, 454 are synchronously operated in the example of FIG. 5 such that the center of the mask 50 is substantially aligned with the axis 445 when coupled with the second end effector 450. Alternatively, the linear actuators 452, 454 may also be asynchronously operated as needed. To further guide and support the motion of each of the linear actuators 452, 454 along the axis 455, the plurality of slides 460 are also coupled to the base plate 451 and are arranged parallel to the axis 455. The cross bracket 456 couples the linear actuator 452 to two of the slides 460, while the cross bracket 458 couples the linear actuator 454 to the remaining two slides 460. Two of the mask strap holding rods 470 extend from each of the cross brackets 456, 458 and the plurality of mask strap holding rods 470 are held mutually parallel to one another. During operation of the linear actuators 452, 454, the distance is varied along the axis 455 between pairs of the mask strap holding rods 470. As previously described, the form correction fixture 300 holds the straps 54 in a stretched position as defined by the holding pins 330 extended positions, and thus the plurality of mask strap holding rods 470 are placed within stretched boundaries of the straps 54 when transferring the mask 50 therebetween. When inserting the mask strap holding rods 470 for transfer, only an end portion of the mask strap holding rods 470 are used such that a gap is maintained between the base plate 451 and the mask 50. Any suitable distance for the gap between the base plate 451 and the mask 50 may be used that will allow visibility of both the internal and external surfaces of the mask 50. It is also anticipated that little or no gap between the base plate 451 and the mask 50 may alternatively be used if a camera lens (not shown) is mounted on the base plate 451 or if mirrors (not shown) are placed between the base plate 451 and the mask 50.

During transfer of the mask 50 between the form correction fixture 300 and the second end effector 450, the second end effector 450 and/or the form correction fixture 300 may be operated to facilitate the transfer. For example, the linear actuators 452, 454 may be operated to spread the spacing between the mask strap holding rods 470 and the tension of the straps 54 can be transferred to the mask strap holding rods 470. Alternatively, the mask strap holding rods 470 may maintain a fixed spacing, while the stepper motors 304, 306 of the form correction fixture 300 are operated to retract the holding pins 330 and again transfer the tension of the straps 54 to the mask strap holding rods 470. Alternatively, both the second end effector 450 and the form correction fixture 300 may be operated together to transfer the tension of the straps 54 to the mask strap holding rods 470.

Referring again to FIG. 1, once the mask 50 is transferred to the second end effector 450, the second robotic arm 400 may be used to lift the mask 50 upward to a position within the view angle of both a camera 114 and a camera 118 of the computer vision system 150. In an example, the horizontal position of the mask 50 is rotated by approximately 45-degrees, or any suitable angle, by the second robotic arm 400 so that both the internal and external side of the mask 50 are directly viewable by the cameras 114, 118. Alternatively, the mask 50 may be viewed by the camera 114, 118 at different times, at different positions, and at different angles as need to fully inspect the internal and external sides of the mask 50. While the cameras 114, 118 are shown in specific positions in the example of FIG. 1, it is anticipate that the cameras 114, 118 may alternatively be placed in other positions that provide line of sight to the internal and external sides of the mask 50 when the mask 50 is held open by the second robotic arm 400.

In some examples, the computer vision system 150 may be configured to analyze the mask 50 to determine whether the mask 50 can be re-used. The computer vision system 150 may classify different visual parameters of the mask 50 for the analysis. The different visual parameters may include impurities, punctures, nose clip damage, and strap damage. The collected visual parameters may be used to determine whether the mask 50 is suitable for recycling and re-use. In some examples, the system may use convolutional neural networks to detect the masks 50, perform pick and place application on the detected mask 50 using robotic manipulators, and classify different physical parameters of the masks to verify whether they are suitable for UVC based disinfection. If the mask 50 is determined to be suitable for reuse and UVC based disinfection, the second robotic arm 400 may be operated to place the mask onto a main conveyor belt (not shown) or onto a loading tray (not shown) that transfers the mask 50 into the sterilizer. In an example, the main conveyor belt may be located adjacent to the system 100 and the second robotic arm 400 may be configured to rotate about the axis 405 when transferring the mask 50. To release the mask 50 from the mask strap holding rods 470, the linear actuators 452, 454 are operated to move the mask strap holding rods 470 towards the axis 445 and thus release the tension on the straps 54. The mask 50 then rests on the main conveyor belt in an open position. Because each mask 50 is handled by the second robotic arm 400 in the same manner, each mask 50 is placed on the main conveyor belt in a consistent open position which ensures consistent line of sight for the applied UVC based disinfection.

Referring again to FIG. 1, alternatively, if the computer vision system 150 determines that the mask 50 is not suitable for reuse and sterilization, the second robotic arm 400 may place the mask 50 onto a rejection conveyor 120. The rejection conveyor 120 then transfers the masks 50 into a rejection bin 122 for storage, later bulk sterilization, and for discarding.

Figure 6:
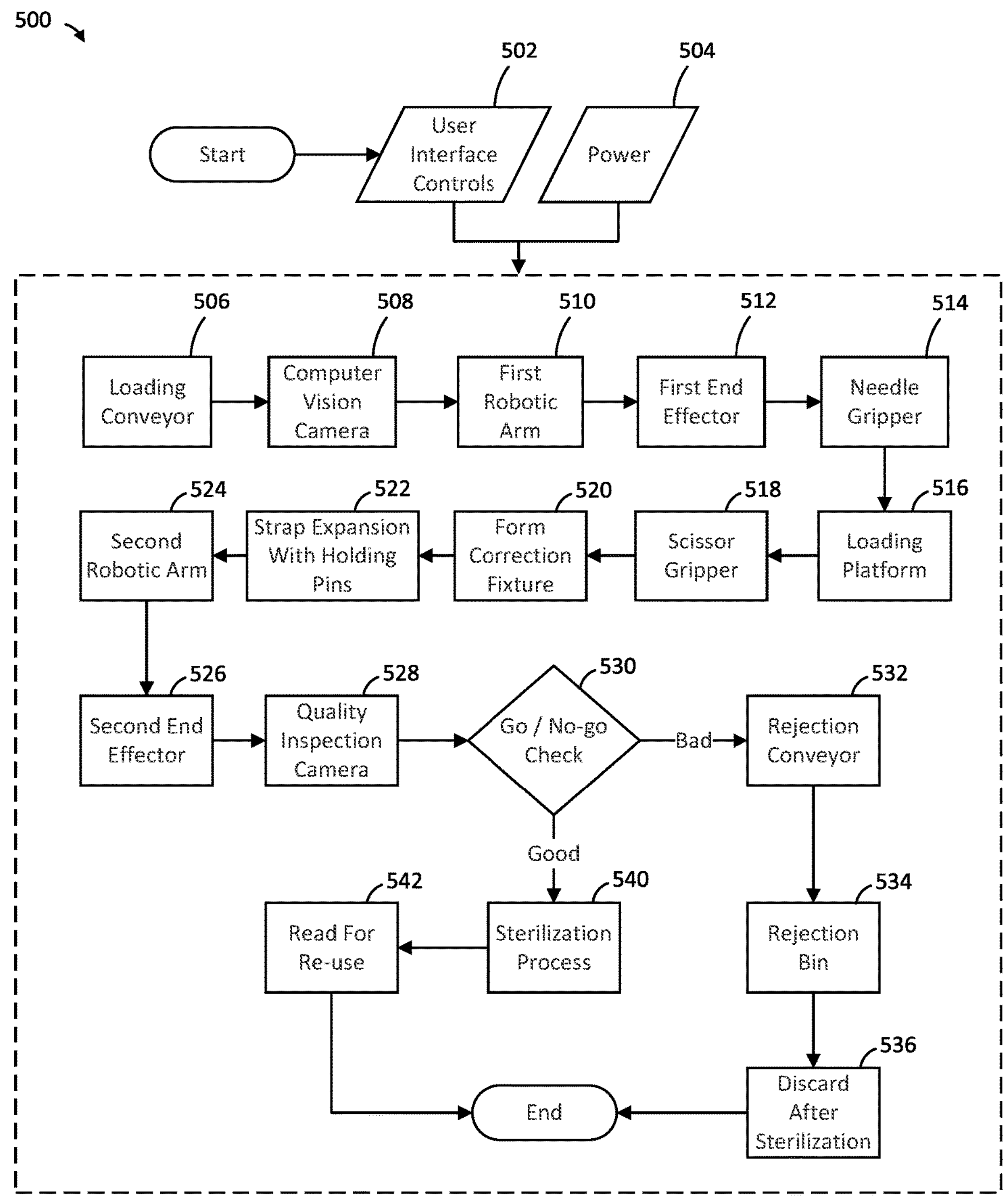
FIG. 6 is a process flow diagram illustrating the steps that may be used to handle and orient a mask to be placed into the disinfection system.

Referring to FIG. 6, a process flow diagram is shown that illustrates the steps that may be implemented into the system 100 and the associated control software. A block 502 provides user interface controls for the system 100 and power is provided by a block 504. A block 506 lists loading the conveyor 110. A block 508 lists use of the computer vision system 150 via the camera 112. In a block 510, the first robotic arm 200 is used via the first end effector 250 of block 512. To use the first end effector 250, the needle gripper 240 is used in block 514 as the mask 50 is placed onto the loading platform 116 in block 516. The scissor gripper 260 is used in block 518 as the first robotic arm 200 is used to place the mask 50 onto the form correction fixture 300 in block 520. The straps 54 of the mask 50 are expanded by the holding pins 330 in block 522. The second robotic arm 400 is used in block 524 via the second end effector 450 of block 526 to grip and transfer the mask 50 away from the form correction fixture 300. Quality inspection of the mask 50 is performed with the cameras 114, 118 of the computer vision system 150 in block 528 and a go/no-go check is performed by the system 100 in decision block 530. Masks 50 that are "bad" are determined to include visual parameters (e.g., such as impurities, punctures, nose clip damage, strap damage, etc.) that make the mask 50 non-suitable for recycling and re-use. Bad masks 50 are transferred to the rejection conveyor 120 in block 532, to the rejection bin 122 in block 534, and are stored for discard after sterilization in block 536. Alternatively, masks determined by the decision block 530 to be "good" are suitable for sterilization and for re-use. Good masks 50 are transferred to a sterilization process in block 540 and are then conditioned and ready for re-use in block 542.

Figure 7:
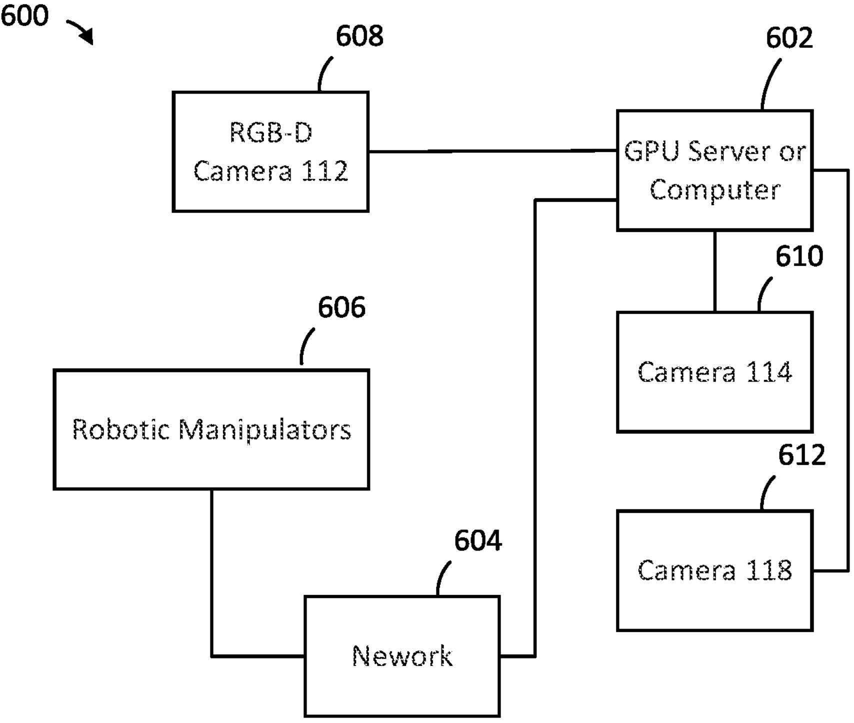
FIG. 7 is exemplary system architecture to operate and control the system of FIG. 1.

Referring to FIG. 7, an exemplary system architecture 600 to operate and control the system 100 of FIG. 1 is illustrated. A GPU or computer is shown by block 602 and is operatively connected with a network as shown in block 604, the camera 114 in block 610, the camera 118 in block 612, and the camera 112 in block 608. The first robotic arm 200 and the second robotic arm 400 are also operatively connected in block 606 to the network of block 604.

Figure 8:
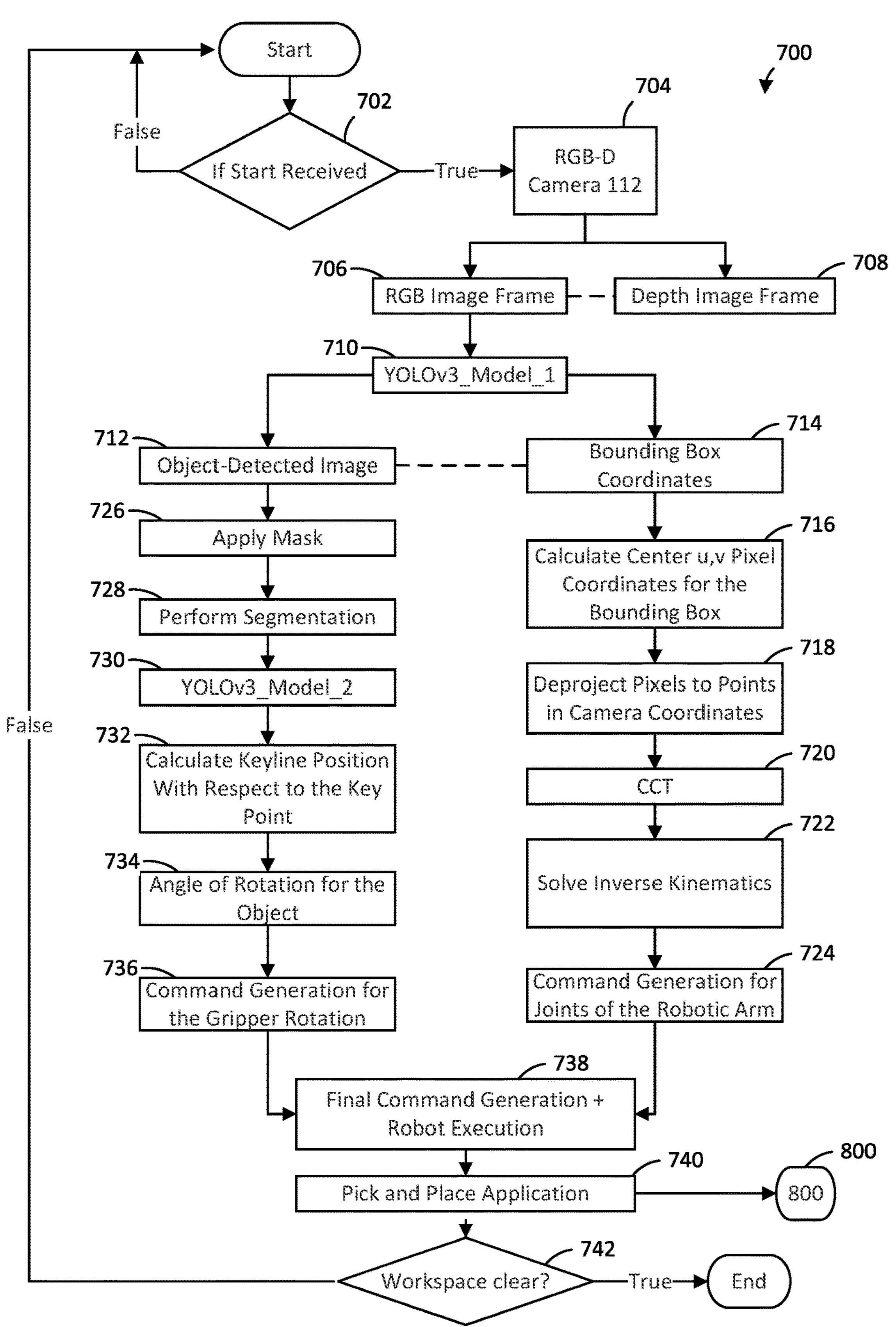
FIG. 8 is a flowchart of a control software that may be used to operate and control the system of FIG. 1.

Referring to FIG. 8, a flowchart or process 700 of the control software to operate and control the system 100 is further illustrated. As detailed herein, machine learning and AI algorithms may be used. In particular, the flowchart of FIG. 8 illustrates how the detection of the mask 50 is achieved by the camera 112 of the computer vision system 150 as shown in FIG. 1. In block 702, the control software receives a start signal to acquire an image from the camera 112 in block 704. In an embodiment, the camera 112 is an RGB-Depth camera interfaced with the computer 602, which stores both "colour image frame" and "depth frame" at the same instance. These two frames are aligned with each other synchronously. The images are saved onto the non-volatile storage of the computer 602 as shown in blocks 706 and 708. The RGB Image frame of size 640×480 is passed as input into the YOLOv3 based neural network model in block 710. The YOLOv3 model is trained on a private dataset-1 containing a large number of training images. This neural network has 53 convolutional layers and is based on Darknet-53. This model renders an output image as shown in block 712 that shows where the object (e.g., the mask 50) is detected in the input image by performing bounding box prediction as shown in block 714. The network predicts four coordinates for each of bounding box tx, ty, tw, th. YOLOv3 predicts an objectness score for each bounding box using logistic regression. Each predicted bounding box use independent logistic classifiers for class prediction and may contain multilabel classification.

The four coordinates for each bounding box are saved on to the non-volatile storage of the computer 602 which is later used to find the centre of the bounding box as shown in block 716. The centre of the bounding box is represented by two coordinates u, v in the image plane. Next in block 718, the values of the centre coordinates are used to project these pixels and other points of interest, into camera coordinates using distortion adjustment, intrinsic, and extrinsic parameters of the RGB-D camera while at the same time aligning them with respect to the depth frame as previously described. In result, three camera coordinates Cx, Cy and Cz (depth) are calculated. In block 720, the camera coordinate transformation (CCT) is applied. The obtained camera coordinates are transformed into robot coordinates by performing Homogenous Transformation which takes into account the rotation and translation of the camera frame. The output of this process provides three robot coordinates which are Rx, Ry, Rz. These values of the robot coordinates are used in block 722 to solve the Inverse Kinematics equation for the first robotic arm 200 as shown in FIG. 1. In particular, the solution of the Inverse Kinematics equation provides joint angles for the lower arm 210, the middle arm 20, the upper arm 230, and the first end effector 250 as shown in FIG. 3. The joint angles J0, J1, J2, J3 are used in the block 724 for the command generation.

Referring still to FIG. 8, after the command generation of the joint angles are completed, in block 726, masks (such as the nose mask 60 and strap mask 62 of FIG. 2B) are applied to the image with detected object to eliminate any unwanted background. The masked image is used to perform segmentation based on colour space as shown in block 728. The resulting segmented image is provided as input to the second YOLOv3 Model shown in block 730. The second YOLOv3 Model uses similar architecture previously described with respect to the first YOLOv3 Model of block 710. The second neural network model based on YOLOv3 operated in the detection of specific key points (e.g., key point 64 of FIG. 2C) and provides feature extraction of the detected object. In the block 732, a feature vector is generated between the detected key points 64. The detected features are later used for calculating the position of the feature vector in order to calculate the orientation angle 68 (FIG. 2D) as shown in the block 734. Once the orientation angle 68 of the object is calculated a command is generated as shown in the block 736 that accounts for the rotation of the needle gripper 240 of the first end effector 250 (FIG. 3), as alternatively describes herein as joint J4 for the first robotic arm 200.

Once both blocks 736 and 724 are complete, final commands are generated in block 738 and the first robotic arm 200 executes these commands. In particular, the first robotic arm 200 lifts the mask 50 from the conveyor 110 and places the mask 50 onto the loading platform 116 as shown in FIG. 1, and as described in block 740. The conveyor is 110 is checked for another mask 50 in the decision block 742 and the process 700 is repeated as needed.

Figure 9:
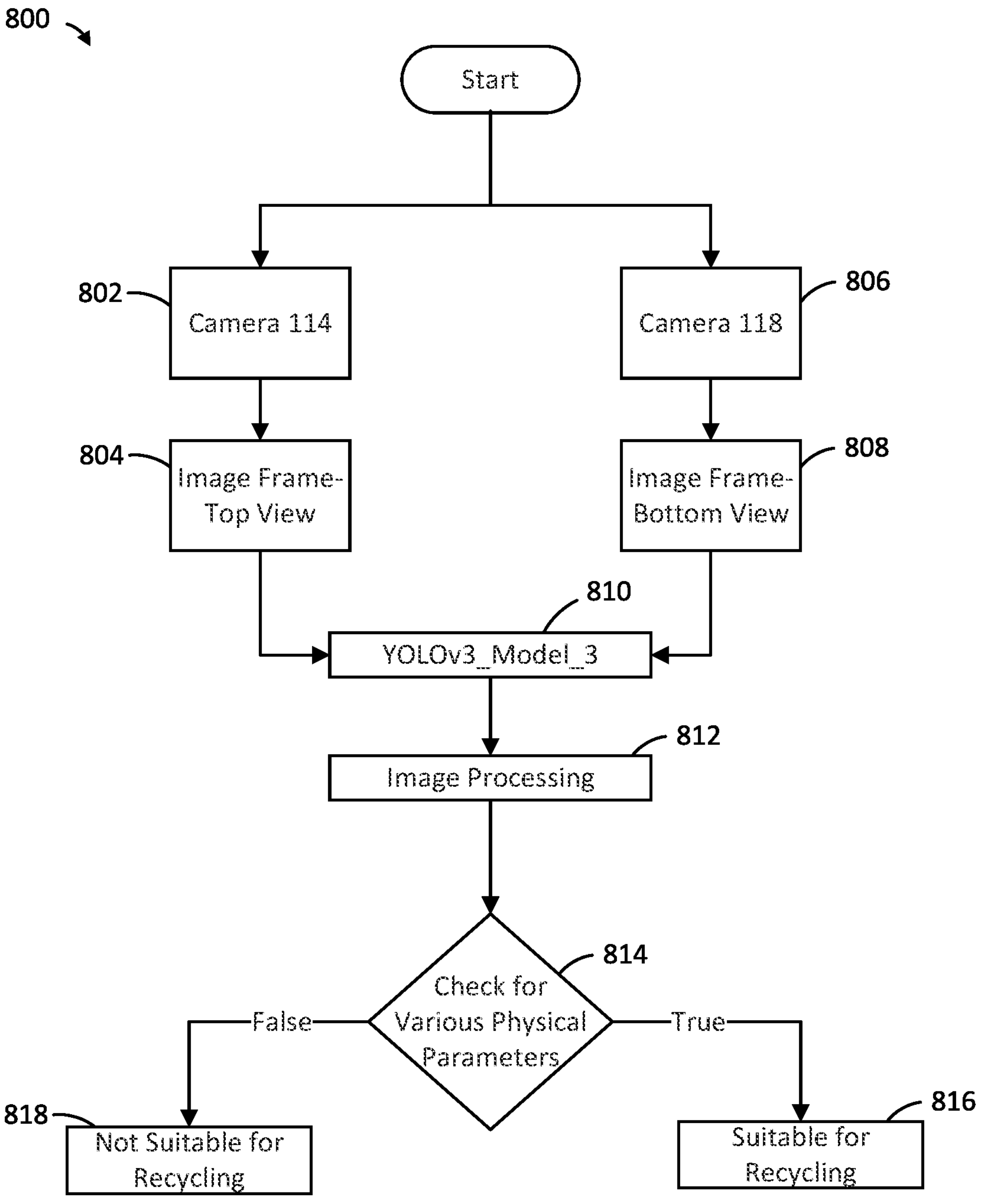
FIG. 9 is another flowchart of a control software that may be used to operate and control the system of FIG. 1.

Referring to FIG. 9, a flowchart or process 800 of the control software to further operate and control the system 100 is further illustrated. As detailed herein, machine learning and AI algorithms may be used. In particular, the flowchart of FIG. 9 illustrates how the computer vision system 150 inspects the masks 50 to determine of the mask 50 is suitable for re-use. In blocks 802 and 804 the camera 114 acquires an image of the external surface of the mask 50, while in blocks 806 and 808 the camera 118 acquires an image of the internal surface of the mask 50. The images from the cameras 114, 118 are RGB types image frames that are passed onto a third YOLOv3 based neural network model as shown in the block 810. This model detects and classifies different parameters such as the mask straps 62, the nose piece 52, presence of any damage or other substances on the mask 50 exterior and interior surfaces. Further image processing techniques are applied as shown in block 812 to enhance the image and to determine if the mask 50 can be recycled or not. In block 814 the two output images are then compared to a custom threshold value to determine if the mask 50 is suitable for recycling and disinfection with UVGI. If the mask is suitable (block 816) for recycling or if the mask is unsuitable (block 818) for recycling the values are stored on the computer 602 for further actions and the mask 50 is moved and sorted by the second robotic arm 400 as detailed herein.

As described the systems and methods described for the system 100 may be used to disinfect 100 masks 50 per day for clinical applications, 10,000 masks 50 per day for hospital applications, and up to 100,000 masks 50 per day for commercial applications. In addition, while masks 50 are described, the system 100 may also be readily used for other personal protective equipment.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A system for handling, inspecting, and orienting a mask to be placed into a disinfection system, the system comprising:

a computer vision system configured to detect a position of the mask position and calculate an orientation angle of the mask;

a first robotic arm configured to lift the mask and adjust the mask position of the mask based on the orientation angle;

a second robotic arm configured to hold open the mask for a visual inspection of an internal and an external surface of the mask; and mask, a form correction fixture configured to stretch and open the mask by applying tension to straps on the mask while supporting a portion of the internal surface with a conical fixture.

2. The system according to claim 1, wherein the computer vision system comprises a plurality of cameras, and wherein the visual inspection of the internal and the external surfaces are performed by the plurality of cameras while the mask is held open in a fixed position.

3. The system according to claim 1, wherein the mask is transferred in a generally flat condition along a conveyor to the first robotic arm.

4. The system according to claim 1, wherein the computer vision system is further configured to classify visual parameters of the mask, wherein the visual parameters comprise at least one of impurities, punctures, nose clip damage, and strap damage.

5. The system according to claim 1, wherein the computer vision system is further configured to analyze the mask to determine whether the mask can be re-used without human intervention.

6. The system according to claim 5, wherein the second robotic arm is further configured to place masks that can be re-used in an open position for transfer to the disinfection system and configured to place masks that cannot be re-used onto a rejection conveyor for transfer to a rejection bin.

7. The system according to claim 1, wherein the computer vision system is further configured to identify a nose piece and a strap using object detection algorithms and configured to apply at least one of a nose mask or a strap mask to omit image details from analysis.

8. The system according to claim 7, wherein the computer vision system is further configured to circumscribe a circle around a perimeter of the mask, identify a key point along the perimeter and a key line between a center of the circle and the key point, wherein a direction of the key line is related to the orientation angle of the mask.

9. A method for handling, inspecting, and orienting a mask to be placed into a disinfection system, the method comprising:
- detecting a position of the mask and calculating an orientation angle of the mask with a computer vision system;
- lifting the mask with a first robotic arm and adjusting the position of the mask based on the orientation angle;
- holding the mask open with a second robotic arm;
- supporting a portion of an internal surface of the mask with a conical fixture;
- applying tension to straps of the mask to stretch and open the mask; and
- inspecting the internal surface and an external surface of the mask via a camera while held open by the second robotic arm.

10. The method according to claim 9, wherein inspecting the internal and the external surfaces is performed by the camera as one of a plurality of cameras, and wherein the mask is held open in a fixed position during visual inspection.

11. The method according to claim 9, further comprising transferring the mask in a generally flat condition along a conveyor to the first robotic arm.

12. The method according to claim 9, further comprising classifying visual parameters of the mask with the computer vision system, wherein the visual parameters comprise at least one of impurities, punctures, nose clip damage, and strap damage.

13. The method according to claim 9, further comprising analyzing the mask with the computer vision system and without human intervention to determine whether the mask can be re-used.

14. The method according to claim 13, further comprising:
- using the second robotic arm to place masks that can be re-used in an open position for transfer to the disinfection system; and
- using the second robotic arm to place masks that cannot be re-used onto a rejection conveyor for transfer to a rejection bin.

15. The method according to claim 9, further comprising:
- identifying a nose piece and a strap using the computer vision system and object detection algorithms; and
- applying at least one of a nose mask or a strap mask to omit image details from analysis.

16. The method according to claim 15, further comprising:
- circumscribing a circle around a perimeter of the mask within the computer vision system;
- identifying a key point along the perimeter and a key line between a center of the circle and the key point; and
- calculating the orientation angle of the mask based on a direction of the key line.

* * * * *